United States Patent [19]

Contestable et al.

[11] Patent Number: 5,460,946
[45] Date of Patent: Oct. 24, 1995

[54] DIAGNOSTIC TEST KIT AND SPECIFIC BINDING ASSAY USING MODULATOR OF SIGNAL RESULTING FROM PEROXIDASE LABEL

[75] Inventors: Paul B. Contestable; Bradley P. Boyer; Brian A. Snyder; Thomas R. Kissel, all of Rochester, N.Y.

[73] Assignee: Eastman Kodak Company, Rochester, N.Y.

[21] Appl. No.: 43,246

[22] Filed: Apr. 6, 1993

Related U.S. Application Data

[63] Continuation-in-part of Ser. No. 773,063, Oct. 8, 1991, abandoned.

[51] Int. Cl.$^6$ .................................................. G01N 33/569
[52] U.S. Cl. .................. 435/7.32; 435/7.9; 435/7.92; 435/28; 435/962; 422/52
[58] Field of Search .................. 435/7.32, 7.9, 435/7.92, 28, 962, 968, 975; 436/518, 528, 530, 534, 808; 422/52

[56] References Cited

U.S. PATENT DOCUMENTS

| 3,427,381 | 2/1969 | Kirkland | 424/54 |
| 3,480,392 | 11/1969 | Carlos | 424/54 |
| 4,661,342 | 4/1987 | Yamazaki et al. | 424/54 |

FOREIGN PATENT DOCUMENTS

| 0328388 | 8/1989 | European Pat. Off. |
| 54-141763 | 5/1979 | Japan . |

OTHER PUBLICATIONS

Schonbaum, *J. Biol. Chem.*, 248(2), pp. 502–511; 1973.
Brooks, *Biochem. Biophys. Res. Comm.*, 116(3), pp. 916–921 (1983).
Nakatani et al., *Biochemistry*, 25, pp. 3515–3518 (1986).
Ator et al., *J. Biol. Chem.*, 262(4), 1542–1551 (1987).
Rich et al., *Biochim. Biophys. Acta.*, 525, 325–337 (1978).
Ikeda–Saito et al., *J. Biol. Chem.*, 266(6), 3611–3616 (1991).
Persijn et al. J. Clin. Chem. Clin. Biochem. 16 (1978) 531–532.
Davies et al. Biochem J. (1989) 258 801–806.
Contestable et al. Abstract 1077 J. Dert. Res. 69 (Special Issue Mar) 1990, 243.
Schael et al. Biochem. Cell Biol. 64 1333–1338 (1986).
Ishikawa et al. Molecular Cellular Probes 5 pp. 81–95 (1991) "Development of ultrasensitive enzyme immunoassay reviewed with emphasis on factors which limit the sensitivity".

*Primary Examiner*—Toni R. Scheiner
*Assistant Examiner*—Lora M. Green
*Attorney, Agent, or Firm*—J. Lanny Tucker

[57] ABSTRACT

The signal generated in a specific binding assay wherein a peroxidase label is used to detect the resulting specific binding complex on a microporous filtration membrane can be modulated by contacting the signal forming reagents with a buffered solution of a hydroxamic acid or acyl hydrazine having the structure $$R-CO-NH-R'$$

or an equivalent salt thereof, wherein R is aryl of 6 to 10 carbon atoms in the aromatic nucleus, alkyl of 1 to 7 carbon atoms or cycloalkyl of 5 to 10 carbon atoms in the ring, and R' is hydroxy or amino. This solution can be provided in a diagnostic test kit for use in various methods to detect a specific binding ligand. The result is improved signal stability and lowered background after the use of a high pH wash solution in the assay.

4 Claims, No Drawings

DIAGNOSTIC TEST KIT AND SPECIFIC BINDING ASSAY USING MODULATOR OF SIGNAL RESULTING FROM PEROXIDASE LABEL

RELATED APPLICATION

This application is a Continuation in Part of U.S. Ser. No. 07/773,063 filed 08 Oct. 1991 by Contestable et al, now abandoned.

FIELD OF THE INVENTION

The present invention relates to a diagnostic test kit comprising a compound which modulates the signal resulting from the action of a peroxidase on its substrate. The invention is also directed to a method for determining a specific binding ligand using, among other reagents, the modulating compound.

BACKGROUND OF THE INVENTION

There is a continuous need in medical practice, research and diagnostic procedures for rapid, accurate and qualitative or quantitative determinations of biological substances which are present in biological fluids at low concentrations. For example, the presence of drugs, narcotics, hormones, steroids, polypeptides, prostaglandins or infectious organisms in blood, urine, saliva, vaginal secretions, dental plaque, gingival crevicular fluid and other biological specimens has to be determined in an accurate and rapid fashion for suitable diagnosis or treatment.

To provide such determinations, various methods have been devised for isolating and identifying biological substances employing specific binding reactions between the substance to be detected (identified herein as a "specific binding ligand") and a compound specifically reactive with that substance (sometimes identified as a "receptor" for the ligand).

The complex formed between ligand and receptor can be detected by a variety of known methods. The most commonly used methods employ a signal-generating moiety of some type which is either already attached to one of the components of the complex, or becomes part of the complex through further reaction. For example, in the formation of a complex of biotin with avidin, the complex may be detected using a label on either the avidin or biotin molecule. Such a label can be a radioisotope or an enzyme conjugated with the avidin or biotin. Alternatively, the avidin-biotin complex might be detected by further reaction with a labeled molecule which is specific to either or both parts of the complex. It is commonly known to do the same with antigens and their corresponding antibodies.

Preferred labels in specific binding reactions are clearly enzymes because the handling and disposal problems associated with radioisotopes can be avoided. Many enzymes are known to be useful in this context with peroxidases being the most common.

In diagnostic tests designed to be rapid and easy to use with moderate training in a doctor's office or clinic, the specific binding ligand of interest (such as an antigen from an infectious agent) is often detected using colorimetric or chemiluminescent signals resulting from reaction of the enzyme label with its corresponding substrate. There is a need to produce the signal quickly and intensely if the ligand is present.

However, there is also a need to have the signal produced in a defined region of a test zone in a test device so an adjacent or surrounding region could be used as a background control. In such cases, production of the signal should be modulated or stopped after a certain period of time in order to provide clear distinction between test zone and background zone.

An advance in the art in the detection of microorganisms associated with periodontal diseases is described and claimed in U.S. Ser. No. 468,392 (filed Jan. 22, 1990 by Snyder). This case describes the simultaneous detection and differentiation of these microorganisms, and particularly *Actinobacillus actinomycetemcomitans*, *Porphyromonas gingivalis* (formerly known in the art as *Bacteroides gingivalis*) and *Prevotella intermedia* (formerly known as *Bacteroides intermedius*), in an assay using water-insoluble reagents in defined regions of a microporous filtration membrane. The simultaneous detection and differentiation of these microorganisms have considerable clinical and commercial significance.

The assay described in this copending application is carried out using peroxidase as a label on antibodies specific for the bacterial antigen. It is well known in such assays to use a buffered solution of sodium azide to stop the production of colorimetric signal when peroxidase reacts with a suitable substrate. In most instances, a low concentration (for example, 0.1 weight percent) of sodium azide performs satisfactorily.

However, it was determined that high pH (9 or more) washings were required to reduce background from nonspecific binding of target antigen with non-specific antibodies. Yet, when high pH wash solutions were used, sodium azide became ineffective to adequately modulate or stop the formation of signal, especially when the signal was detected on a porous microporous filtration membrane. In other words, the colorimetric signal production is only slowed down slightly by the azide and is not stopped. This causes the specific signal and the surrounding region on the membrane to continue to develop signal thereby reducing the ease of interpretation and preventing accurate quantitation of positive results. It is desired to prevent this from happening, yet it is uncertain as to why the high pH wash affects the function of the sodium azide. However, it appears that the interaction of the membrane and the absorbent underneath it allows high pH wash solution to flow back into the region where signal is generated and the function of the azide is impaired.

It was considered to use greater concentrations of sodium azide and strong low pH buffers to solve the problem, but this was not acceptable because sodium azide is a well known toxic material and also has explosive properties.

SUMMARY OF THE INVENTION

The noted problem has been solved using a diagnostic test kit comprising, separately packaged:

(a) a buffered composition comprising at least about 0.05 weight percent of a compound having the structure

wherein R is aryl of 6 to 10 carbon atoms in the aromatic nucleus, alkyl of 1 to 7 carbon atoms, or cycloalkyl of 5 to 10 carbon atoms in the ring, and R' is hydroxy or amino, (b) a water soluble, peroxidase-labeled specific binding species, (c) a wash solution comprising a water-soluble surfactant, the solution being buffered to a pH of at least 9, and (d) a disposable test device containing a microporous filtration membrane for capture and detection of a specific binding ligand.

This test kit can be used to practice a method for the determination of a specific binding ligand comprising:

A. reacting a specific binding ligand from a biological specimen with a water-soluble receptor specific for the ligand, the receptor being labeled with peroxidase, to form a peroxidase-labeled specific binding complex between the ligand and receptor, B. prior to, simultaneously with or subsequently to step A, insolubilizing the specific binding ligand so as to provide an insolubilized specific binding complex, C. simultaneously with or subsequently to step B, capturing the insolubilized specific binding complex on a microporous filtration membrane, D. washing the captured insolubilized specific binding complex with a wash solution comprising a water-soluble surfactant, the solution being buffered to a pH of at least 9, E. contacting the washed insolubilized specific binding complex on the microporous filtration membrane with a composition for providing a colorimetric or chemiluminescent signal in response to peroxidase in the complex, F. modulating the level of the signal by contacting the washed insolubilized specific binding complex on the membrane with a composition comprising at least about 0.05 weight percent of a compound having the structure

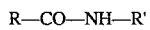

R—CO—NH—R' wherein R is aryl of 6 to 10 carbon atoms in the aromatic nucleus, alkyl of 1 to 7 carbon atoms, or cycloalkyl of 5 to 10 carbon atoms in the ring, and R' is hydroxy or amino, and G. detecting the signal as an indication of the amount or presence of the specific binding ligand in the biological specimen.

The invention provides an effective means for modulating or stopping the production of a colorimetric or chemiluminescent signal produced by enzymatic reaction in specific binding assays. This effectiveness is particularly apparent when peroxidase is the enzyme of concern. In assays carried out on a microporous membrane, unwanted colorimetric signal from reagents on or above the membrane, or from reagents that flow back through the membrane is virtually eliminated, and the assay can be used semi-quantitatively. The invention is particularly useful to modulate the signal when high pH washings are used.

These advantages are achieved by contacting the insolubilized specific binding complex, having a peroxidase label therein, with a hydroxamic acid or acyl hydrazine as defined herein. Depending upon the concentration of modulating compound used, the production of signal from the enzymatic reaction with its substrate can be stopped completely or modulated to slow the reaction rate.

DETAILED DESCRIPTION OF THE INVENTION

The compounds used in the practice of this invention are hydroxamic acids or acyl hydrazines represented by the following structure:

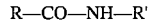

R—CO—NH—R' or an equivalent salt thereof wherein R' is hydroxy or amino. When R' is hydroxy, these compounds can also be in the form of hydroximic acids [that is, R—C(=NOH)OH], and can exist in two isomeric forms.

In this structure, R can be substituted or unsubstituted aryl of 6 to 10 carbon atoms in the aromatic nucleus, including but not limited to phenyl, naphthyl, tolyl, o-, m- or p-methoxyphenyl, 3-amino-2-carbamoylphenyl and 3-amino-2-carboxyphenyl, metal or ammonium salt. When R is aryl, it is preferably phenyl, 3-amino-2-carbamoylphenyl, or 3-amino-2-carboxyphenyl, metal or ammonium salt, and most preferably phenyl.

However, R can also be substituted or unsubstituted alkyl of 1 to 7 carbon atoms, including but not limited to methyl, ethyl, isopropyl, butyl, pentyl, hexyl, 2-methylpentyl and heptyl, or substituted or unsubstituted cycloalkyl of 5 to 10 carbon atoms in the ring, including but not limited to, cyclopentyl, cyclohexyl and cycloheptyl. R can also be an unsubstituted or substituted aromatic heterocyclyl of 5 to 10 atoms (at least one of which is oxygen, sulfur or nitrogen, and the remainder are carbon atoms) in the aromatic ring. Useful aromatic heterocyclyl groups include, but are not limited to, pyrrolyl, pyrazolyl, imidazolyl, triazolyl, tetrazolyl, thienyl, furyl, thiazolyl, oxazolyl, benzimidazolyl, benzothiazolyl, benzoxazolyl, pyridyl, quinolyl, pyridizinyl, pyrimidyl, triazinyl, indolyl and quinoxalinyl.

Preferably, R is phenyl, substituted or unsubstituted alkyl of 1 to 4 carbon atoms, cycloalkyl of 5 or 6 carbon atoms in the ring or an aromatic heterocyclyl of 5 or 6 nuclear carbon and heteroatoms. Most preferably, R is phenyl or 3-amino-2-carbamoylphenyl or 3-amino-2-carboxyphenyl, metal or ammonium salt. Preferred compounds are benzohydroxamic acid and equivalent salts.

For all of the acids described herein, equivalent salts include, but are not limited to, ammonium salts, alkali metal salts, alkaline earth metal salts and other salts readily apparent to one skilled in the art.

The hydroxamic acids defined above can be readily prepared using known starting materials and chemical synthetic methods such as the reaction of hydroxylamine with acyl halides and other methods described, for example, by March, *Advanced Organic Chemistry: Reactions, Mechanisms and Structure,* McGraw-Hill, 1968 and later editions, Schonbaum, *J.Biol.Chem,,* 248(2), pp. 502–511, 1973 and references mentioned therein, and Brooks, *Biochem. Biophys.Res.Comm,,* 116(3), pp. 916–921, 1983 and references mentioned therein. Benzohydroxamic acid is available from a number of commercial sources.

The acyl hydrazines described herein can be prepared generally by condensation of an anhydride, particularly a phthalic anhydride such as 3-nitrophthalic anhydride, with hydrazine hydrate. The acylhydrazine obtained in this exemplary reaction can be hydrolyzed with base, and hydrogenated in the presence of palladium on carbon. If ammonia is employed as the base, the product obtained is the 2-carbamoyl derivative. Otherwise, a 2-carboxylate salt is obtained. The preparation of a specific acyl hydrazine, namely N-(3-amino-2-carboxybenzoyl)hydrazine, sodium salt is described in detail in copending U.S. Ser. No. 773,065 (filed on Oct. 8, 1991 by Snodgrass et al) now U.S. Pat. No. 5,252,457.

The compound described herein is provided in a buffered solution at a concentration of at least about 0.01 percent based on total solution weight. The upper limit of the amount of acid can be as high as is necessary to achieve the desired signal modulation. However, in practicality, the amount reaches a point where no more acid is needed to modulate a given amount of peroxidase in the assay. Generally, the amount of compound is in the range of from about 0.01 to about 5 weight percent, with from about 0.05 to about 1 weight percent being preferred. A mixture of hydroxamic acids or salts can be used if desired.

Generally, the hydroxamic acid or acyl hydrazine described herein is buffered to a pH of from about 6 to about 11 using one or more suitable buffers including, but not limited to, phosphate, 3-(4-morpholino)propanesulfonic acid, 2-(4-morpholino)ethanesulfonic acid, glycine and others readily apparent to one skilled in the art. Phosphate buffered saline solution is preferred to provide a pH of from about 7 to about 8.

Addenda which may optionally be included in the buffered composition of compound include inorganic salts, surfactants and polymeric materials.

The buffered composition described above is generally supplied as part of a diagnostic test kit having a number of separately packaged reagents, compositions and equipment needed for a given assay. However, the buffered composition can be provided by itself or prepared at the time of the assay. Typical diagnostic kit components, however, include a water-soluble peroxidase-labeled specific binding species, wash solution, extraction compositions, signal-providing compositions, disposable test devices and others readily apparent to one of ordinary skill in the art.

The test kit particularly includes a wash solution useful to remove uncomplexed materials from the specific binding complex formed in the assay of this invention. The wash solution comprises one or more water-soluble surfactants (usually anionic or nonionic) and is buffered to a pH of 9 or more (preferably 9 to 12) using one or more suitable buffers.

Useful surfactants in the wash solution include anionic materials such as carboxylate and sulfonate salts (for example, alkylbenezenecarboxylates, alkylbenzenesulfonates, alkylsulfonates, sulfosuccinate ester salts, formalin condensates of naphthalene and alkylnaphthalenesulfonates), sulfate ester salts (for example, alkylsulfate ester salts, polyoxyalkylene alkyl ether sulfate ester salts or polyoxyalkylene alkylaryl ether sulfate ester salts) and phosphate ester salts (for example, alkyl phosphate ester salts, polyoxyalkylene alkyl ether phosphate ester salts or polyoxyalkylene alkylaryl ether phosphate ester salts). Others, including cholic acid and salts thereof are well known.

Preferred anionic surfactants are those represented by the structure:

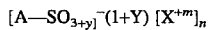

$$[A\!-\!SO_{3+y}]^{-(1+Y)} [X^{+m}]_n$$

wherein A is a hydrocarbon having a molecular weight of at least about 180, $X^{+m}$ is hydrogen or a monovalent or divalent cation, m is 1 or 2, y or 0 or 1, and n is 1 or 2 provided that m and n are not both 2. Further details of such materials are provided in U.S. Ser. No. 773,065 (noted above). A most preferred anionic surfactant for use in the wash solution is TERGITOL™ 4 anionic surfactant.

Useful nonionic surfactants include, but are not limited to, alkylolamides, polyoxyalkylene alkyl or alkyl aryl esters, polyoxyethylene and polyoxypropylene polyols, polyoxyalkylene fatty acid esters, polyoxyalkylene alkylamines, and polyhydric alcohol type surfactants such as polyhdyric alcohol fatty acid esters. Various other useful nonionic surfactants are well known in the art.

The specific binding species in the test kit can be any molecule from a biological or chemical source which reacts specifically with a ligand of interest. For example, the species can be avidin or a derivatized form thereof, biotin or a derivatized form thereof, antibody, antigenic material, a hapten, sugar, lectin or other chemical or biological compound which has a receptor as that term is understood in the art. In the context of this invention, a nucleic acid is also considered a specific binding species which "complexes" (or hybridizes) with a complementary nucleic acid which is considered a ligand in this instance.

Preferably, the water-soluble peroxidase-labeled species included in the test kit is an antibody specific to an antigen or antigenic material of interest. For example, the antigen can be derived from any viral, bacterial or cellular source, and polyclonal or monoclonal antibodies specific thereto can be produced using known immunization and hybridoma technologies. Many such antibodies are also commercially available. Preferably, the species is labeled with a horseradish peroxidase but peroxidases from any of animal, plant, fungal or bacterial source can also be used. Many such enzymes are commercially available. Procedures for attaching peroxidase to specific binding species are also well known (including for example, Yoshitake et al, *Eur. Biochem,*, 101, pp. 395–399, 1979).

The method of this invention can be used to determine, quantitatively or qualitatively, a specific binding ligand of interest. Such ligands include, but are not limited to, oligonucleotides, nucleic acids, proteins, carbohydrates, lipopolysaccharides, peptides, polypeptides, polysaccharides, glycolipids, glycoproteins and any components of these materials. Such ligands can be detected in any human or animal biological fluid or specimen including, but not limited to, whole blood, sera, plasma, lymphatic fluid, bile, urine, spinal fluid, seminal fluid, vaginal secretions, sputum, perspiration, stool specimens, tissue preparations, dental plaque, saliva, gingival crevicular fluid, semen and other sources readily apparent to one skilled in the art. The invention is particularly useful for the detection of microorganisms associated with periodontal diseases found in saliva, dental plaque, gingival crevicular fluid and other oral fluids or specimens.

In particular, the microorganisms *Actinobacillus actinomycetemcomitans, Prophyromonas gingivalis* and *Prevotella intermedia* are determined, either individually or collectively, using the present invention. However, other microorganisms which are suspected of being associated with periodontal diseases can also be detected or differentiated with this invention. Such other microorganisms include, but are not limited to, *Campylobacter rectus, Bacteroides forsythus, Eikenella corrodens, Fusobacterium nucleatum* and *Treponema denticola*. In some embodiments, it is irrelevant as to which serotypes of any of the microorganisms may be present. In other embodiments, the invention can be used to differentiate among serotypes of a single species as well as among species. Presently at least three serotypes of each of the three primary microorganisms have been isolated and identified in this art. However, it is believed that this invention can similarly be used in the detection of other serotypes once they are known.

Before considering the first step of the method of this invention, it should be understood that prior to step A there can be a wide variety of procedures carried out for specimen preparation, purification or extraction of antigen or nucleic acid. For example, generally antigens to be detected in an assay are extracted from the microorganism or host cell in a suitable fashion. A preferred extraction procedure for providing detectable antigens from microorganisms associated with periodontal diseases is described below, but this invention is not to be construed as limited to it. Nucleic acid extraction from cellular materials may also be necessary, and a great number of procedures are known in the art.

One useful procedure which can be carried out to increase the sensitivity of nucleic acid detection is known in the art as polymerase chain reaction (PCR). The details of this process are provided for instance, in U.S. Pat. No. 4,683,202 (issued Jul. 28, 1987 to Mullis). Once a nucleic acid has been amplified by this technique, various detection means can be employed including the use of a peroxidase-labeled probe. The enzyme label can then be used for providing an appropriate detectable signal which can be modulated using the present invention. While this particular embodiment is not illustrated in the working examples, a worker skilled in the art would be able to provide such an example with routine experimentation in view of the teaching available in the art and that provided herein.

In the practice of this invention, the specific binding ligand in a biological specimen (or a ligand obtained therefrom) is reacted with a water-soluble receptor specific for the ligand. The receptor is labeled with a peroxidase as noted above. A specific binding complex which is labeled with the enzyme is thereby formed. Complex formation typically occurs in solution, but the type of container or vessel in which it occurs is not critical. In some cases, the complex is formed in the crude specimen after lysis or other extraction procedures. In other cases, the complex is formed on a special substrate, plate or membrane which can "capture" the complex in some manner.

Contact can occur at a wide range of temperatures, for example from below room temperature to those near the boiling point of water as long as the components of the complex are not adversely affected. Generally, the contacting is carried out in a range of from about 15° to about 30° C. with room temperature more likely. The reagents are contacted by mixing in some fashion so there is opportunity for the reactants to form the complex. The timing for contact can vary from a few seconds to a few hours depending upon how long complex formation may take, the temperature and other factors known in the art.

Prior to, simultaneously with or subsequently to step A, the specific binding ligand is insolubilized so the resulting complex is also insolubilized and can be removed from solution in a suitable manner. This means that the format for the assay can be of a wide variety of forms that have been developed over the years, and this invention is not limited to any one of them although there are preferred formats noted below.

In one embodiment, a specific binding ligand (for example an extracted antigen) can be insolubilized by direct adsorption or covalent attachment to a solid material, such as polymeric or glass particles, filtration membranes, cellulosic filter papers, solid polymeric or resin-coated films, glass slides or walls of test tubes, glass or polymeric cuvettes and other materials readily apparent to one of ordinary skill in the art. Such assays are generally known in the art as "direct binding" assays whereby the specific binding ligand directly binds to the material, and peroxidase-labeled receptor molecules (such as antibodies) are used to complex with the insolubilized ligand. Alternatively, the receptor can be unlabeled and a second receptor which is labeled with peroxidase and specific to the first receptor can then be used. Detection of the complex can be effected after washing using the high pH wash described above. Further details of how direct binding assays are carried out are provided for example in U.S. Pat. 4,497,899 (issued Feb. 5, 1985 to Armstrong et al) and copending U.S. Ser. No. 468,045 (filed Jan. 22, 1990 by Snyder et al) U.S. Pat. No. 5,212,061.

Examples of other useful assays include competitive immunoassays and enzyme-linked immunosorbent assays (commonly known as ELISA). Such assays are described generally in U.S. Pat. No. 4,427,782 (issued Jan. 24, 1984 to Caldwell et al) and by Schmeer et al, *J.Clin.Microbiol.*, 15(5), pp. 830–834 (1982). Other details are available in Rose et al (Eds.), *Manual of Clinical Laboratory Immunology*, 3rd Edition, American Society for Microbiology, Washington, D.C., 1986, Chapter 74 (Fucillo et al). These assays basically use peroxidase-labeled receptor molecules in various ways depending upon the means of complex insolubilization.

A preferred embodiment of this invention is an immunometric or sandwich assay in which the extracted ligand (for example, an antigen) is reacted at different epitopic sites with two receptor molecules (such as antibodies), one of which is labeled with peroxidase, and the second being immobilized (or capable of being immobilized such as through avidin-biotin complexation). Suitable materials on which one receptor is immobilized include, but are not limited to, particulate carrier materials formed from organisms, natural or synthetic polymers, glass, ceramics, diatomaceous earth or magnetizable particles, microtiter plates, glass slides or tubes, membranes, polymeric or cellulosic papers or films and others known to one skilled in the art. Preferably, particulate materials are used. These particles are more preferably polymeric, spherical in shape and have an average particle size (in largest dimension) of from about 0.01 to about 10 μmeters, although the size, structural and spatial configurations are not critical. The general procedures for immunometric assays are described, for example, in U.S. Pat. No. 4,376,110 (issued Mar. 8, 1983 to David et al) and U.S. Pat. No. 4,486,530 (issued Dec. 4, 1984 to David et al).

The insolubilizable receptors used in the immunometric assays can be attached to water-insoluble materials by physical or chemical means, including adsorption or covalent reaction with reactive groups on the surface of the materials. Covalent attachment is preferred for better assay sensitivity. Many useful reactive groups are known in the art, which groups can be part of the chemical structure of the carrier material, or added by coating or chemical treatment of an inert material. One skilled in the art would readily understand how to prepare such materials to have any of the following reactive groups: carboxy, 2-substituted ethylsulfonyl, vinylsulfonyl, vinylcarbonyl, epoxy, aldehyde, active halo atoms, amino, hydrazide and active esters such as succinimidoxycarbonyl.

Particularly useful particulate materials are polymeric beads which are described, for example, in EP-A-0 323 692 (published Jul. 12, 1989) and which are prepared from one or more ethylenically unsaturated polymerizable monomers having an active halo atom, activated 2-substituted ethylsulfonyl or vinylsulfonyl groups. Other particularly useful particles having reactive carboxy groups are described in U.S. Pat. No. 5,147,777 (Sutton et al)

Procedures for attaching antibodies or other biological materials to particles having reactive groups are well known, as described for example in U.S. Pat. No. 3,925,157 (issued Dec. 9, 1975 to Hamsher), U.S. Pat. No. 4,181,636 (issued Jan. 1, 1980 to Fischer), U.S. Pat. No. 4,703,018 (issued Oct. 27, 1987 to Craig et al) and EP-A-0 323 692. In general, the receptors are mixed with the particles under suitable conditions depending upon the attachment form (adsorption, covalent reaction directly or by use of a linking group). A worker skilled in the art would readily know what conditions should be used for each procedure. For example, for attachment to particles having reactive halo atoms, activated 2-substituted ethylsulfonyl or vinylsulfonyl groups, the receptors are generally mixed with the particles for up to 24 hours at a temperature of from about 20° to about 40° C. in a suspension buffered at a pH of from about 7 to about 10. If carboxy groups are used for attachment, the well known carbodiimide activators can be used, as well as carbomoylonium compounds which are described in EP-A-0 308 235 (published Apr. 22, 1989). Receptors can be absorbed on particles by incubating them with particles in suspension at suitable temperature for several hours.

More preferably, the insolubilized receptors described above are coated or deposited on a microporous filtration membrane which is inert to chemical or biological reactions. It is generally composed of one or more natural or synthetic substances which have sufficient integrity for reagents to react or be affixed thereto without loss of form or function. It is porous enough for filtration needed to remove substantially all uncomplexed materials from the complexes formed thereon. Useful membrane materials include, but are not limited to, porous natural or synthetic polymers, sintered glass, membranes of glass or polymeric films or fibers, ceramic materials, cellulosic materials and particulate structures composed of beads bound together with an adhesive or binder material. The membranes are generally flat, but some irregularities in the surfaces are acceptable, as well as some curvature if it is desired. One skilled in the art would be able to identify other useful materials which are commercially available or prepared using known techniques. Particularly useful materials are treated or untreated polyamide microporous membranes such as those commercially available from Pall Corp. under the trademarks LOPRODYNE and BIODYNE.

The membrane generally has an average pore size in the largest dimension of from 0.5 to about 5 μmeters, although smaller or larger pores would be acceptable as long as the complexes formed remain on the membrane and fluid drainage is not adversely affected.

If desired, the membrane can be coated with surfactant or nonimmunoreactive protein (such as casein or succinylated casein), as known in the art to reduce nonspecific interactions or to promote desired filtration.

The water-insoluble receptors can be affixed to the membrane over its entire surface or in defined regions thereof. Affixation is accomplished using any mechanical means such as coating, dipping, printing or spraying or fixed by covalent means. Generally, they are coated and dried on the membrane prior to use. They can be used in admixture with hydrophilic binders to provide additional integrity to the coating.

The membrane can be hand held in the assay to provide sites for complexation of extracted ligand and receptor thereon. However, preferably, the membrane is disposed or mounted in a disposable test device or article having a suitable frame and structure for holding the membrane and fluid which is drained therethrough. Many such test devices are known in the art, including but not limited to those shown in U.S. Pat. No. 3,825,410 (issued Jul. 23, 1974 to Bagshawe), U.S. Pat. No. 3,888,629 (issued Jun. 10, 1975 to Bagshawe), U.S. Pat. No. 3,970,429 (issued Jul. 20, 1976 to Updike), U.S. Pat. No. 4,446,232 (issued May 1, 1984 to Liotta), U.S. Pat. No. 4,833,087 (issued May 23, 1989 to Hinckley), U.S. Pat. No. 4,847,199 (issued Jul. 11, 1989 to Snyder et al), U.S. Pat. No. 4,921,677 (issued May 1, 1990 to Hinckley et al) and U.S. Pat. No. 4,923,680 (issued May 8, 1990 to Nelson). Particularly useful test devices are those marketed by Eastman Kodak Company under the trademark SURECELL test devices.

Preferred test devices have three test wells designed for providing both negative and positive control results as well as a specimen test result. Each test well has a membrane situated therein.

As noted above, the receptor can also be designed for being insolubilized using a specific binding complex such as avidin-biotin, a sugar with a lectin or others known in the art. Avidin-biotin reactions are preferred in these embodiments because of the high affinity the components have for each other. The receptor molecule to be insolubilized can be biotinylated (such as a biotinylated antibody or nucleic acid), and before, during or after its reaction with the ligand, it can be complexed with avidin which is attached to a solid material (described above). Useful details of such materials and procedures are described, for example, in U.S. Pat. No. 4,870,007 (issued Sep. 26, 1989 to Smith-Lewis).

The insolubilized complex is captured on a microporous filtration membrane followed by washing (step D) the complex with the high pH wash solution described herein to remove uncomplexed materials.

Following washing, the complex is contacted (step E) with a composition suitable for providing a colorimetric or chemiluminescent signal in response to the peroxidase label in the complex. Such a composition can merely be a substrate for peroxidase which is reacted upon to provide the desired signal. More likely, it is two or more reagents which function in one or more reactions to provide the signal. The particular reagents needed would be readily apparent to one skilled in the art since there is considerable art describing reagents which are catalyzed by peroxidase to form dye or chemiluminescent signals. Generally, the composition includes hydrogen peroxide and a compound which provides a signal in response thereto.

For example, a number of leuco dyes are known to be useful for this purpose including those described in U.S. Pat. No. 4,089,747 (issued May 16, 1978 to Bruschi) and U.S. Pat. No. 4,670,386 (issued Jun. 2, 1987 to Babb et al). A preferred dye-providing composition is illustrated in the examples below.

Alternatively, the peroxidase can be used in one or more reactions to produce a chemiluminescent signal, such as described for example in U.S. Pat. No. 4,647,532 (issued Mar. 3, 1987 to Watanabe et al), U.S. Pat. No. 4,835,101 (issued May 30, 1989 to Kao et al), U.S. Pat. No. 4,729,950 (issued Mar. 8, 1988 to Kricka et al) and U.S. Pat. No. 4,598,044 (issued Jul. 1, 1986 to Kricka et al).

The colorimetric or chemiluminescent signal produced can be evaluated visually or with suitable equipment known in the art for this purpose. Normally, it is evaluated and measured with the equipment and compared to standards previously determined.

The advantage of the present invention is effective modulation (changing or stopping completely) of the signal produced using the composition of the hydroxamic acid described above (step F). This is done by contacting the complex producing the signal with the composition at a suitable time after signal production has begun. Generally, this contact occurs within at least about 2 minutes after dye signal begins, and preferably after from about 60 to about 75 seconds. At this point, a dye signal exists but its intensity stops increasing. For a chemiluminescent signal, the composition stops the production of light from the complex.

The method of this invention can be carried out over any suitable period of time with at least about 3 minutes being the minimal time necessary. Generally, the assay (steps A-G) is carried out in from about 3 to about 60 minutes. Except for temperature conditions noted above for individual steps, generally the assay is carried out at from about 15° to about 40° C. with room temperature being preferred. These features are desired but not critical in the practice of the invention.

The method may include a number of optional steps not specifically enumerated in the generic procedure including, but not limited to additional wash steps, extraction steps, filtration steps and others known to one skilled in the art of immunoassays or hybridization assays. Preferably, the method is carried out using a disposable test device and a kit of the necessary components, reagents and equipment using a protocol which is outlined in the accompanying instructions. More preferably, the method is carried out to detect microorganisms associated with periodontal diseases as noted above.

Thus, in a preferred embodiment, a method for the determination of a microorganism selected from the group consisting of *Actinobacillus actinomycetemcomitans, Bacteroides forsythus, Prophyromonas gingivalis* or *Prevotella intermedia* comprises:

A. contacting a specimen suspected of containing an antigen extracted from any of *Actinobacillus actinomycetemcomitans, Bacteroides forsythus, Porphyromonas gingivalis* or *Prevotella intermedia* with a water soluble antibody specific for the extracted antigen, the antibody being labeled with peroxidase, to form a peroxidase-labeled immunological complex between the extracted antigen and antibody, B. prior to, simultaneously with or subsequently to step A, insolubilizing the extracted antigen by reaction with an insolubilized, unlabeled antibody specific to the extracted antigen so as to provide an insolubilized immunological complex, C. simultaneously with or subsequently to step B, capturing the insolubilized immunological complex on a microporous filtration membrane, D. washing the captured insolubilized immunological complex with a wash solution comprising a water-soluble surfactant, the solution being buffered to a pH of at least 9, E. contacting the washed insolubilized immunological complex on the microporous filtration membrane with a composition for providing a colorimetric or chemiluminescent signal in response to peroxidase in the complex, F. modulating and detecting the level of the signal by contacting the washed insolubilized complex on the microporous filtration membrane with a composition comprising at least about 0.01 to about 5 weight percent of a hydroxamic acid or acyl hydrazine as described above, and G. detecting the signal as an indication of the amount or presence of the extracted antigen.

The following example is included to illustrate the practice of this invention, and are not meant to be limiting in any way. All percentages are by weight unless otherwise noted.

Materials and Methods for Example and Comparative Assays

SURECELL™ disposable test devices were used containing LOPRODYNE™ nylon microporous filtration membranes (1.2 μmeters average pore size) incorporated into the three test wells. The membrane was used without any further treatment.

A dye-providing composition was prepared to include 4,5-bis(4-methoxyphenyl)-2-(3,5-dimethoxy-4-hydroxyphenyl)imidazole leuco dye (0,008%), poly(vinyl pyrrolidone) (1%), sodium phosphate buffer (10 mmolar, pH 6.8), hydrogen peroxide (10 mmolar), 4'-hydroxyacetanilide (5 mmolar) and diethylenetriaminepentaacetic acid (10 μmolar).

Polyclonal antibodies directed against each of the three microorganisms *Actinobacillus actinomycetemcomitans* (A.a.), *Prevotella intermedia* (P.i.) and Porphyronomas gingivalis (P.g.) were prepared by intravenous injection of rabbits according to the protocol described in U.S. Ser. No. 468,393 (filed Jan. 22, 1990 by Reynolds et al) now abandoned. This procedure generally included injecting the rabbits with an immunizing amount of antigen a first time, injecting the animals a second time between the second and fourteenth days after the first injection with a boosting amount of the antigen. Beginning the fifteenth day after the first injection, the rabbits were injected at least three times every seven day period for at least four seven-day periods with a boosting amount of antigen. After the last booster injection, antisera was removed from the rabbits. IgG fractions were prepared by ammonium sulfate precipitation, and stored at 4° C. in phosphate buffered saline solution (0.3–0.4% solution). The bacterial strains used to produce the antisera were supplied as viable cultures by H. S. Reynolds (SUNY, Buffalo School of Dentistry). Isolates were subcultured on anaerobic plates. The microorganisms were those identified by the deposit numbers of ATCC 43717, ATCC 43718 and ATCC 43719 for A.a. (serotypes A, B and C), ATCC 25611, NCTC 9336 and ATCC 49046 for P.i. (serotypes A, B and C) and ATCC 33277, 53978 and 53977 for P.g. (serotypes A, B and C). ATCC is the American Type Culture Collection in Rockville, Md., and the NCTC is the National Collection of Type Cultures in London, England.

Water insoluble reagents were prepared by covalently binding antibodies specific to each microorganism (all of serotypes A, B and C) to polymeric particles (1 μmeter average diameter) of Poly[styrene-co-4-(2-chloroethylsulfonylmethyl)styrene] (95.5:4.5 molar ratio) which had been prepared using the procedures of EP-A-0 323 692 (noted above). Covalent attachment was achieved by adding the antibodies (0.75 mg/ml for P.g., total serotypes, and 0.52 mg/ml for A.a. and P.i., total serotypes) to a solution of borate buffer (0.05 molar, pH 8.5) in a test tube and mixing well. The polymeric particles (3% solids) were added to the buffered mixture, and the resulting suspension was rotated end-over-end for 4–24 hours at room temperature to allow covalent attachment of the antibodies to the particles. The suspension was then centrifuged at 2800 RPM for 10 minutes. The supernatant was discarded and the pellet was suspended in glycine buffer (0.1%, pH 8.5) containing merthiolate (0.01%).

A coating suspension of the reagent described above (0.35% solids) was prepared to have polyacyrylamide binder (5%), TWEEN™ 20 nonionic surfactant (0.1%), merthiolate (0.01%) and UVITEX™ optical brightener (0.0005%, Ciba-Geigy) in glycine buffer (0.1 molar, pH 8.5). Each reagent directed to a distinct antigen was coated in defined regions of the membrane in the test devices described above.

Enzyme-antibody conjugates were prepared using antibodies directed to each microorganism conjugated to horseradish peroxidase using the procedure of Yoshitake et al, *Eur. J. Biochem.*, 101, 395, 1979. Each conjugate composition comprised the conjugates (5.6–11.25 μg of each per ml) added to a solution of casein [0.05%, from a 1% solution in 0.05 molar phosphate buffered saline solution, pH 7], TWEEN™ 20 nonionic surfactant (0.3%), merthiolate (0.01%), 4'-hydroxyacetanilide (10 mmolar) and LONZAINE™ C amphoteric surfactant (0.0035%, Lonza Corp.). The amount of antibody specific for A.a. (all serotypes) and P.g. (all serotypes) was 7.5 μg/ml. For P.i. (serotypes A and C), the amount was 5.6 μg/ml, and for serotype B it was 11.25 μg/ml.

Wash solution A comprised TERGITOL™ 4 anionic surfactant (1.35%) in glycine buffer (0.1 molar, pH 10) containing casein (0.5%) and merthiolate (0.01%).

Wash solution B comprised TERGITOL™ 4 anionic surfactant (2.7%) in sodium phosphate buffer (pH 7.2).

Wash solution C comprised sodium decyl sulfate (1.8%) in sodium phosphate buffer (0.1 molar, pH 7.3).

Antigen extraction was accomplished using a solution of EMCOL TM CC-9 cationic surfactant (5%, Witco Chemical Co.), sodium dodecyl sulfate (5%) in glycine buffer (0.1 molar, pH 8.5).

All other reagents were obtained from Eastman Kodak Company or other well known suppliers of chemicals and reagents.

EXAMPLE

Use of Various Compositions to Modulate or Stop Dye Signal

This example demonstrates the practice of this invention and the use of a benzohydroxamic acid to modulate the formation of a dye signal using a peroxidase-labeled antibody.

Extraction and Assay Protocol

Antigen extraction was accomplished by mixing the microorganism specimen with the extraction solution noted above (450 µl) for about 1 minute at room temperature. The amount of cells in the final solutions was $7 \times 10^5$ cells/ml of P.g.

The assays were carried out by adding a sample (450 µl) of extractant provided by the extraction procedure noted above to each test well of the disposable test device as described above. Fluid was allowed to drain through the membranes in the test wells as the extracted antigen complexed with the immunological reagent (containing antibodies) on the membranes.

Immediately, the conjugate of peroxidase and antibody (80 µl) was added to the test wells and sandwich complex formation was allowed to proceed by incubation at room temperature for about 2 minutes. Each test well was then half filled with the wash solution A (about 500 µl) which then drained through the membrane. This was repeated once.

After the last wash, the dye-providing composition (120 µl) was added to each test well followed by a 1 minute incubation at room temperature.

At the end of this incubation period, the "stop" solution was added to modulate the formation of dye signal, and the signal was visually evaluated by comparing it to a color score card having density values of 1 to 10 with 10 representing the highest density. A density score was also given to the background on the membrane where no dye should appear.

The "stop" solutions evaluated were as follows:

Control A: sodium azide (0.1%) in phosphate buffered saline solution (0.05 molar, pH 7.3).

Control B: sodium azide (0.1%) in 3-(4-morpholino)propanesulfonic acid (1 molar, pH 7).

Control C: sodium azide (0.1%) in 2-(4-morpholino)ethanesulfonic acid (1 molar, pH 6).

Control D: sodium azide (1%) in 3-(4-morpholino)propanesulfonic acid (1 molar, pH 7).

Control E: sodium azide (1%) in 2-(4-morpholino)ethanesulfonic acid (1 molar, pH 6).

Control F: citric acid (1 molar, pH 4).

Control G: citric acid (1 molar, pH 3).

Control H: citric acid (1 molar, pH 2).

Control I: ethanolamine (1 molar, pH 10).

Control J: ethanolamine (1 molar, pH 11).

Control K: sodium azide (0.1%), poly(vinylpyrrolidone) (6.25%) and TERGITOL™ 4 anionic surfactant (0.1%) in 2-(4-morpholino) ethanesulfonic acid (1 molar, pH 6).

Invention: benzohydroxamic acid (0.1%) in phosphate buffered saline solution (0.05 molar, pH 7.3).

Table I below shows the time (minutes) after the addition of "stop" solution at which dye development due to non-specific binding was observed. This is undesirable binding of the labeled antibody in the region of the membrane removed from the complex. It can be seen that the "stop" solution containing the benzohydroxamic acid according to this invention provided the longest time before a dye signal from nonspecific binding was observable.

TABLE I

| "Stop" Solution | Time (Minutes) |
|---|---|
| Control A | 4–5 |
| Control B | 4–5 |
| Control C | 6 |
| Control D | 7 |
| Control E | 15 |
| Control F | 4–5 |
| Control G | 7 |
| Control H | 45 |
| Control I | 10 |
| Control J | 10–15 |
| Control K | 6–10 |
| Invention | >60 |

Table II below quantitates the area of the membrane affected by non-specific binding after the formation of dye signal after certain periods of time. The values of "1+" to "4+" refer to the intensity and size in area of development of dye signal on the membrane with a value of 1+ referring to a small portion of the membrane being affected with low dye signal, and a value of 4+ referring to the entire membrane having a very high dye signal. These data indicate that only the present invention consistently provided no undesired dye signal over the entire period of the test (1 hour).

TABLE II

| | "Stop" Solutions | | | | | | | | | | | |
|---|---|---|---|---|---|---|---|---|---|---|---|---|
| Time (Min.) | Control A | Control B | Control C | Control D | Control E | Control F | Control G | Control H | Control I | Control J | Control K | Example 1 |
| 0 | 0 | 0 | 0 | 0 | 0 | 0 | 0 | 0 | 0 | 0 | 0 | 0 |
| 5 | 3+ | 3+ | 0 | 0 | 0 | 1+ | 0 | 0 | 0 | 0 | 0 | 0 |

TABLE II-continued

| | "Stop" Solutions | | | | | | | | | | | |
|---|---|---|---|---|---|---|---|---|---|---|---|---|
| Time (Min.) | Control A | Control B | Control C | Control D | Control E | Control F | Control G | Control H | Control I | Control J | Control K | Example 1 |
| 10 | 4+ | 4+ | 2+ | 2+ | 0 | 3+ | 1+ | 0 | 2+ | 0 | 1+ | 0 |
| 15 | 4+ | 4+ | 3+ | 3+ | weak | 4+ | 2+ | 0 | 4+ | 3+ | 3+ | 0 |
| 30 | 4+ | 4+ | 4+ | 4+ | 2+ | 4+ | 3+ | 0 | 4+ | 4+ | 4+ | 0 |
| 45 | 4+ | 4+ | 4+ | 4+ | 2+ | 4+ | 3+ | weak | 4+ | 4+ | 4+ | 0 |
| 60 | 4+ | 4+ | 4+ | 4+ | 3+ | 4+ | 3+ | weak | 0 | 0 | 4+ | 0 |

Table III below shows the dye signal generated in response to the presence of P.g. (serotype B, 7×10$^5$ cells/ml) after certain times for certain "stop" solutions. The assay carried out according to this invention provided the most stable dye signal after 15 minutes. The dye signals were evaluated on a scale of 1 to 10 with 10 representing the highest dye density.

TABLE III

| | "Stop" Solutions | | | | | | |
|---|---|---|---|---|---|---|---|
| Time (Min.) | Control A | Control E | Control G | Control H | Control J | Control K | Invention |
| 0 | 5 | 5 | 5 | 5 | 5 | 5 | 5 |
| 5 | 5 | 5 | 5 | 4–5 | 2–3 | 5 | 5 |
| 10 | U | 5 | 4–5 | 3 | U | 5 | 5 |
| 15 | U | 4 | 4 | 1 | U | U | 5 |

U = unable to evaluate

In summary, the data indicate that the use of benzohydroxamic acid to modulate or stop the formation of dye signal according to this invention is quite successful. Not only is the dye signal stabilized over a long period of time, but it unexpectedly eliminates the background signal caused by the backflow of reagents through the membrane on which the signal is generated. This allows the user of this assay sufficient time to evaluate the dye signal and provides for semi-quantitative results since there is less background and a more stable signal.

Comparative Assays: Comparisons of Stop Solutions Using Different Wash Solutions These comparative assays are essentially taken from Example 1 of copending and commonly assigned U.S. Ser. No. 07/774,019 (filed Oct. 8, 1991 by Boyer, Contestable and Snyder) now U.S. Pat. No. 5,248,595. Wash solutions A, B and C (noted above) were used in the assays.

Antigen from ATCC 53978 (serotype B, P.g.) was extracted by subjecting the cells to the extraction composition noted above for less than one minute at room temperature to achieve a final concentration of 1.25×10$^8$ total cells/ml.

The resulting extract (450 µl) was filtered through a 1.2 µmeter membrane and added to one test well of a test device as described above. The microporous filtration membrane of the test device had defined regions of reagents specific for each of A.a., P.g. and P.i. Fluid was allowed to drain through the membrane in the test well. Antibody conjugate composition (80 µl) was immediately added to each test well followed by incubation for two minutes at room temperature (about 20°–25° C.). Either wash solution A, B or C (500 µl) was then added to each test well and allowed to drain, followed by a second application of wash solution A, B or C (500 µl).

Dye-providing composition (80 µl) was added to each test well. After a one minute incubation at room temperature, the dye stop solution containing sodium azide (0.1%) in phosphate buffer (pH 7.2) was added. The dye signal was then visually evaluated and compared to a calibrated color chart containing reflectance density values. The reflection densities were then converted to transmission density ($D_T$) using the Williams-Clapper transformation [see J. Optical Soc. Am., 43, p. 595 (1953)]. $D_T$ values of 0.003 or less correspond to a visual evaluation of "no dye signal".

The results are shown below in Table IV. Antigen to P.g. alone was being targeted for detection, so the results show the cross-reactivity of the extracted target antigen with other antibody reagents in the test device.

TABLE IV +HC,8 +UZ,8/32 D+HD T +L Dye Signal?

| Assay Wash | P.g. Reagent | P.i. Reagent | A.a. Reagent |
|---|---|---|---|
| A | 0.101 | 0.003 | 0.003 |
| B | 0.114 | 0.005 | 0.007 |
| C | 0.114 | 0.024 | 0.024 |

The results of Table IV indicate that cross-reactivity can be effectively eliminated using the high pH wash solution described by our colleagues Boyer et al in U.S. Ser. No. 07/774,019 (noted above) U.S. Pat. No. 5,248,595.

However, as noted above, it was observed that sodium azide was not always effective to modulate or stop the formation of dye signal when a high pH wash solution was used. In many cases, because the wash solution was able to flow back through the microporous membrane on which the immunoassay takes place (identified as "backwash"), the sodium azide solution became ineffective. It was initially considered that the concentration of sodium azide could be increased, but that created additional problems of toxicity and potential explosive properties of the azide. Thus, we found there was a need for a different means for stopping the dye signal formation without the use of sodium azide when the high pH wash solution was used in the immunoassay. The result is the present invention, as described above, and illustrated in the Example above.

The invention has been described in detail with particular reference to preferred embodiments thereof, but it will be understood that variations and modifications can be effected within the spirit and scope of the invention. All patents, patent applications (published or unpublished, domestic or foreign), scientific literature, books and other prior art cited herein are each incorporated herein by reference for the teaching therein pertinent to this invention.

We claim:

1. A method for the determination of a microorganism selected from the group consisting of *Actinobacillus actinomycetemcomitans, Bacteroides forsythus, Porphyromonas gingivalis* and *Prevotella intermedia* comprising:

A. contacting a specimen suspected of containing an antigen extracted from a microorganism selected from the group consisting of *Actinobacillus actinomycetemcomitans, Bacteroides forsythus, Porphyromonas gingivalis* and *Prevotella intermedia* with a water soluble antibody which specifically binds to said extracted antigen, said antibody being labeled with peroxidase, to form a peroxidase-labeled immunological complex between said extracted antigen and antibody, B. prior to, simultaneously with or subsequently to step A, insolubilizing said extracted antigen by reaction with an insolubilized, unlabeled antibody which specifically binds to said extracted antigen so as to provide an insolubilized immunological complex, C. simultaneously with or subsequently to step B, capturing said insolubilized immunological complex on a microporous filtration membrane, D. washing said captured insolubilized immunological complex with a wash solution comprising a water-soluble surfactant, said solution being buffered to a pH of 9 to 12, E. contacting said washed insolubilized immunological complex on said microporous filtration membrane with a composition for providing a colorimetric or chemiluminescent signal in response to peroxidase in said complex, said composition comprising either; a leuco dye and hydrogen peroxide, or luminol and hydrogen peroxide, F. modulating the level of said signal by contacting said washed insolubilized immunological complex on said microporous filtration membrane with a composition comprising at least about 0.01 to about 1 weight percent of benzohydroxamic acid, wherein said modulating is carried out within about 2 minutes after step E, and G. detecting said signal as an indication of the amount or presence of said extracted antigen.

2. The method of claim 1 wherein said peroxidase is horseradish peroxidase.

3. A diagnostic test kit comprising, separately packaged:

(a) a buffered solution of benzohydroxamic acid present in an amount of from about 0.01 to about 1 weight percent, (b) either:
      (i) a leuco dye composition comprising a leuco dye and hydrogen peroxide, or
      (ii) a luminol composition comprising luminol and hydrogen peroxide, (c) a wash solution comprising a water-soluble surfactant buffered to a pH of from 9 to 12, (d) a water-soluble, peroxidase labeled antibody which specifically binds to a microorganism selected from the group consisting of *Actinobacillus actinomycetemcomitans, Bacteroides forsythus, Porphyromonas gingivalis* and *Prevotella intermedia,* and (e) a disposable test device containing a microporous filtration membrane for capture and detection of an immunoreagent.

4. The kit of claim 3 wherein said peroxidase is horseradish peroxidase.

* * * * *